United States Patent [19]
Keller et al.

[11] Patent Number: 5,898,503
[45] Date of Patent: Apr. 27, 1999

[54] SURFACE PLASMON RESONANCE SENSOR WITH INTERCHANGEABLE OPTICAL ELEMENT

[75] Inventors: Robert C. Keller; Jose L. Melendez, both of Plano; Richard A. Carr, Rowlett, all of Tex.

[73] Assignee: Texas Instruments Incorporated, Dallas, Tex.

[21] Appl. No.: 09/072,656

[22] Filed: May 5, 1998

Related U.S. Application Data

[63] Continuation of application No. 08/820,730, Mar. 19, 1997, abandoned.

[51] Int. Cl.⁶ .................................................. G01N 21/17
[52] U.S. Cl. ............................................................. 356/445
[58] Field of Search ..................... 356/318, 445, 356/446, 317, 345; 422/82.05, 82.11, 82.09, 68.1, 88, 61, 82.06, 83, 91; 436/139–142, 144, 164, 165, 170, 171, 113, 121, 131

[56] References Cited

U.S. PATENT DOCUMENTS

| | | | |
|---|---|---|---|
| 4,602,869 | 7/1986 | Harrick | 346/244 |
| 4,886,357 | 12/1989 | Harrick | 356/300 |
| 5,064,619 | 11/1991 | Finlan | 422/82.05 |
| 5,322,798 | 6/1994 | Sadowski | 436/113 |
| 5,443,890 | 8/1995 | Ohman | 428/167 |
| 5,485,277 | 1/1996 | Foster | 356/445 |

FOREIGN PATENT DOCUMENTS 0 517 930 A1  12/1992  European Pat. Off. .
WO 91/13339  9/1991  WIPO .
WO 92/14140  8/1992  WIPO .

OTHER PUBLICATIONS

Melendez, J. et al., "A Commercial Solution for Surface Plasmon Sensing", Sixth International Meeting on Chemical Sensors, Gaithersburg, MD, USA, Jul. 1996, Sensors and Actuators B (Chemical), vol. B35, No. 1–3 ISSN 0925–4005, Elsevier, Switzerland, Sep. 1996, pp. 212–216.

Garabedian, R., "Microfabricated Surface Plasmon Sensing System", 7th International Conference on Solid State Sensors and Actuators (Transducers '93), vol. A43, No. 1–3, ISSN 0924–4247, Yokohama, Japan, Jun. 7–10, 1993.

*Primary Examiner*—Frank G. Font
*Assistant Examiner*—Michael P. Stafia
*Attorney, Agent, or Firm*—David Denker; Christopher L. Maginniss; Richard L. Donaldson

[57] ABSTRACT

A surface plasmon resonance (SPR) sensor includes a transparent base housing 12 and a detachable optical housing 19. Radiation from a radiation source 10, disposed within base housing 12, is polarized by polarizing filter 16 and passes through the interface between base housing 12 and optical housing 19. The polarized radiation 18 is reflected from a mirror 20 onto a SPR layer 22, which is formed on an exterior surface of optical housing 19. Layer 22 comprises a thin layer of a conductive material. Radiation 24 reflected from SPR layer 22 re-enters housing 19 and strikes an array 28 of photodetectors. From the intensity of radiation at each photodetector, one can determine the index of refraction of the substance on the opposite side of SPR layer 22.

13 Claims, 3 Drawing Sheets

SURFACE PLASMON RESONANCE SENSOR WITH INTERCHANGEABLE OPTICAL ELEMENT

This application is a continuation of application Ser. No. 08/820,730, filed Mar. 19, 1997 now abandoned.

FIELD OF THE INVENTION

This invention relates broadly to the field of optical sensors and, more particularly to the field of sensors used in the fields of chemical, biochemical, biological or biomedical analysis, process control, pollution detection and control, and other similar areas.

BACKGROUND OF THE INVENTION

Surface plasmon resonance is an optical surface phenomenon that has been employed in sensors used in the fields of chemical, biochemical, biological or biomedical analysis. A surface plasmon is a surface charge density wave at the surface of a thin conducting film. A description of this phenomenon is found in the article by H. Raether in Physics Thin Films, 1977, 74 pp 237–244. This resonance can be observed when a polarized beam of monochromatic light is totally internally reflected from a dielectric interface having a thin metal film formed thereon. Usually the interface comprises a smooth surface of a transparent body such as glass. The light internally reflected by the interface has a minimum intensity at a particular angle referred to as a resonant angle in the literature. This angle is determined by the dielectric conditions adjacent the metal film and the properties of the film itself.

In prior sensors utilizing surface plasmon resonance, a thin metal film (SPR film) is usually applied to a flat surface of a glass prism. The resonance angle is determined by directing a polarized light beam through the prism onto the surface with the metal film thereon and measuring the intensity of the light reflected therefrom and through an external surface of the prism. Such arrangements, however, require a very high degree of precision in order to manufacture and align the separate optical parts so as to be able to produce accurate measurements. Additionally, such arrangements are not readily adapted to changing the prism to eliminate problems of contamination or to change the physical configuration to detect different materials.

The basis for the use of surface plasmon resonance for sensing is the fact that the oscillation of a surface-plasma of free electrons which exists at a conductor-dielectric boundary is affected by the refractive index of the material adjacent the conducting film surface on the side thereof opposite the prism. For a given wavelength of radiation, the resonance occurs when the angle of incidence of the polarized radiation has a particular value and this value is dependent on the refractive index of the material adjacent the film. As such, changes in the refractive index give rise to changes in the angle at which surface plasmon resonance occurs. When polarized light strikes the thin metal film at the "resonance angel", the intensity of the reflected light therefrom is minimized. Hence, by detecting the angle at which this minimum occurs, the refractive index of the material adjacent the film can be determined. The usefulness of this approach, however, has been limited due to system complexity related primarily to mechanical alignment issues associated with separate components.

SUMMARY OF THE INVENTION

The problems associated with earlier sensors are overcome by the present invention which includes a structure with a detachable optical portion of the sensor. A base housing is made of a material which is transparent to the radiation produced by a radiation source. The radiation source produces light that passes through the base housing and into a detachable housing where the radiation strikes an exterior surface of the housing on which a thin conducting layer (SPR film) is formed. The light reflected from the conducting layer is directed toward an array of radiation detectors disposed in the base housing. The detector having the minimum output level is associated with radiation rays from the source that have bounced off the thin metal layer at the "resonance" angle which is a function of the refractive index of the material contacting the conducting layer. Suitable index matching liquids or the like are located between the base housing and the detachable optical portion to minimize the deflection of the radiation which passes from the base housing to the detachable optical portion or vice versa.

BRIEF DESCRIPTION OF THE DRAWINGS

The above mentioned objects, advantages and features of this invention are described below in connection with the drawings wherein.

DETAILED DESCRIPTION

Figure 1:
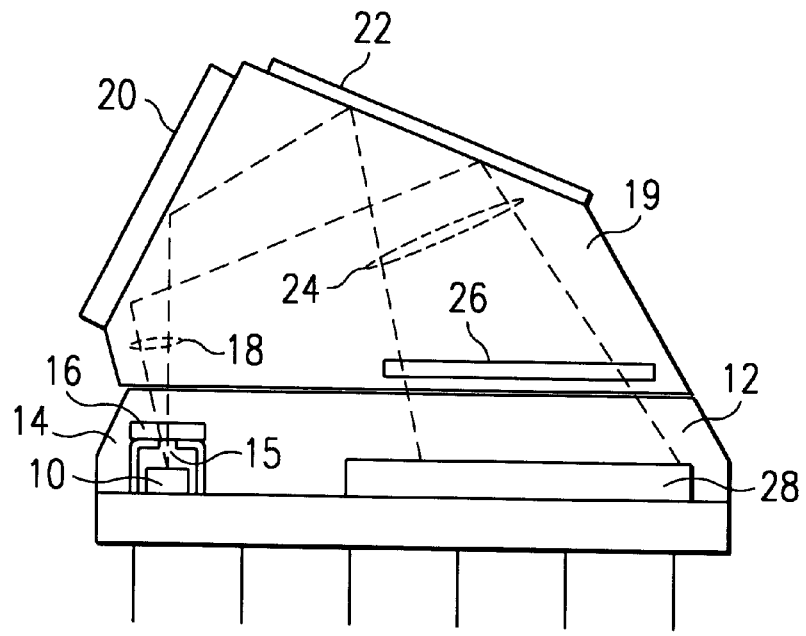
FIG. 1 illustrates the present invention with a base housing on which a detachable optical housing is disposed.

FIG. 1 illustrates one embodiment of the present invention. In this configuration, a radiation source 10, which may comprise a light emitting diode (LED), a laser diode or any other suitable source of radiation, is disposed within a base housing 12. The housing 12 is made of a material which is transparent to the radiation from the source 10 such as suitable plastics or epoxy. In particular, an epoxy marketed under the trademark Epocast® 2013 Parts A/B by Furane Products Company has been found useful especially for radiation sources in the infrared range. Other usable materials include Emerson & Cumming, Stycast 1269A Parts A/B, Tracon Trabond F114, Dexter Hysol OS1000, Norland 61 and 63, Dexter Hysol MG18 or nitto 8510-1100. Other usable materials include polymethylmethacrylate or polycarbonate.

A light shield 14 is disposed around the source 10 to prevent stray radiation from being directed throughout the sensor. The shield 14 has an aperture 15 which allows radiation from the source 10 to pass therethrough in a generally vertical direction. A polarizing filter 16 is disposed above the aperture 15 for producing polarized radiation. There are many suitable polarizers such as the plastic polarizing material sold by Polaroid Corporation known as HN7 Linear Polarizer. By reason of the fact that the radiation source 10 acts somewhat like a point source of radiation, the polarized radiation rays 18 (light rays) diverge from each other.

The diverging polarized radiation 18 passes through the interface between the base housing 12 and the detachable optical housing 19 which rests on the upper surface of the housing 12. The optical housing 19 is made of a material which transmits radiation from the source 10 and may be of the same or other material as the material used for the housing 12. The radiation rays 18 reflect internally from a planar mirror 20 which is disposed so that the plane thereof is not normal to the direction to the polarized radiation 18. The diverging polarized radiation 18, after being reflected from the mirror 20, is directed toward a surface plasmon resonance (SPR) layer 22 which is formed on an exterior surface of the optical housing 19.

The surface plasmon resonance layer 22 comprises a thin layer of a conductive material such as copper, silver or gold having a substantially uniform thickness. The layer 22 is preferably planar although other configurations, such as convex or concave configurations, or featured with steps, periodic or non-periodic, can also be utilized. This layer 22, in one embodiment of the invention, comprises a film of gold approximately 275 angstroms thick. The thickness of a surface plasmon resonance layer may vary from about 200 to about 600 angstroms and still permit surface plasmon resonance to occur. The specific film thickness is determined by experimentation with respect to the frequency of the radiation for the source 10 and the properties of the conductive material used for layer 22. As is known in the art, when radiation strikes a thin conductive film at the interface of an insulator, the intensity of reflection therefrom is a function of the angle of incidence of the radiation onto the film and the refractive index of the material in contact with the other side of the film. Hence, by determining the angle at which minimum reflectance occurs, it is possible to determine the index of refraction of the material on the side of the film opposite the side the radiation is reflected from.

In accordance with utilizing the principal of operation described above, the configuration of FIG. 1 produces diverging radiation 24 which is reflected from the thin surface plasmon resonance layer 22. The diverging radiation 24 passes through a spectral filter 26 prior to exiting the housing 19. Thereafter, the radiation 24 enters the housing 12 and strikes a detector array 28. For optical radiation, the detector array 28 comprises an array of photodetectors. Each detector in the array 28 produces a signal on an output pin with an electrical signal that is proportional to the intensity of the radiation striking the detector. By measuring the voltage at each detector and knowing the angle that the radiation striking that detector intercepted the surface plasmon resonance layer 22, one can produce a plot of reflected radiation intensity as a function of the angle. That plot can be correlated to the index of refraction of the substance on the side of the surface plasmon resonance layer 22 opposite the side which reflects the radiation.

Those of skill in the art will recognize that the physical location of the elements illustrated in FIG. 1 can be moved or relocated while retaining the function described above. For example, the location and shape of the mirrors utilized for reflecting the radiation could take on other configurations and locations so long as radiation strikes a surface plasmon resonance layer and the intensity of the radiation reflected therefrom is measured as a function of the angle of the radiation striking the surface plasmon resonance layer.

Figure 2:
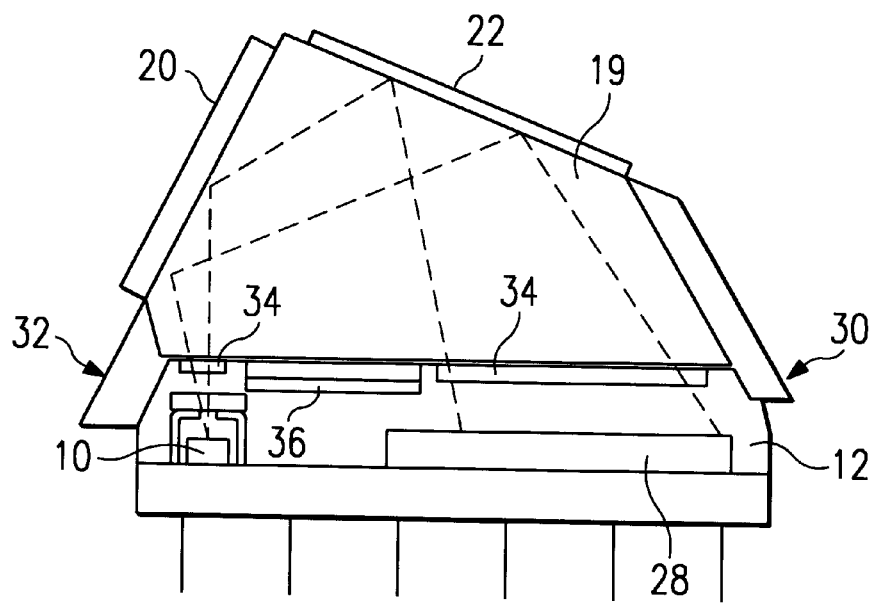
FIG. 2 illustrates one embodiment of the present invention wherein polarized light rays are diverging from each other prior to contacting a surface plasmon resonance layer.

FIG. 2 illustrates an alternative configuration to that illustrated in FIG. 1. This alternative configuration includes a housings 12 and 19. The housing 19 of FIG. 2, however, includes downwardly projecting wing portions 30 and 32 which fit over the walls of the housing 12 when the two housings 12 and 19 are placed in a position as illustrated. The wing projections 30 and 32 assure that the housing 19 is properly aligned with housing 12 so that radiation from the source 10 will ultimately strike the sensor 28 after bouncing off the mirror 20 and the SPR surface 22. Indeed, the housings 12 and 19 can be thought of as being self-aligning because the wing projections 30 and 32 assure proper alignment.

Those of skill in the art will recognize that whenever a beam of light passes from one medium to another in a non-normal direction, the direction of the beam leaving the junction on one side thereof usually leaves at an angle different from the angle the radiation enters the junction. This phenomenon is caused by the fact that the index of refraction of the body/gas on one side of the junction is different from the index of refraction of the of the gas/body on the other side of the junction. In the configuration of FIG. 1 and 2 of the present invention, since the housing 12 and 19 are usually made of the same material, the fact that the light passing through the junction from one housing 12 to the other housing 19, for example, passes through a gaseous medium causes the direction of the radiation to change due to the fact that the gas trapped between the housings 12 and 19 does not have the same index of refraction as the housings 12 and 19. To correct this, an index of refraction matching fluid may be located between the housings 12 and 19. The fluid should have about the same index of refraction as that of the housings 12 and 19. When doing this for the configuration of FIG. 1, the fluid would be placed over the surfaces of the housings 12 and 19 prior to locating them as shown therein. Some of the fluid will naturally be pressed out of the area between the housings. The escape of such fluid, however, can be prevented by having a gasket or the like disposed between the housings 12 and 19 to make sure that the index matching fluid will not escape from therebetween.

FIG. 2 presents an alternative to the configuration of FIG. 1. In this configuration, pockets 34 are formed in the upper surface of the base housing 12. These pockets 34 are positioned so that the light passing between the housings 12 and 19 will pass through these pockets 34 as viewed in FIG. 2. Between the pockets 34 is an overflow pocket 36. When the housings 12 and 19 are being assembled as shown in FIG. 2, the pockets 34 are first filled with an index matching fluid. Then the housings 12 and 19 are placed together as shown. Because there is an empty pocket 36 between the housings 12 and 19, the excess fluid readily flows from the housings 12 and 19 into the pocket 34 thereby leaving the housings 12 and 19 in contact with the index matching fluid in the regions therebetween through which light passes. Since the index of refraction of this fluid is the same as that for the housings 12 and 19, the junction between these bodies does not cause any deviation of the light path as it passes from one housing to another. As such, the index matching fluid provides a means for minimizing the deviation of the direction of the radiation path which occurs at the boundary between base housing 12 and the detachable optical housing 19.

Figure 3:
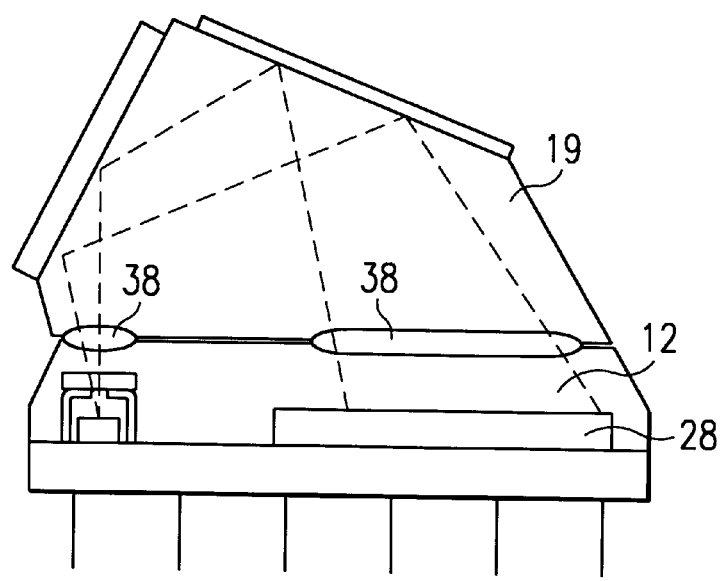
FIG. 3 illustrates an alternative configuration with index equalizing "pillows" disposed between the base and the detachable optical housing.

A further alternative design is illustrated in FIG. 3. In this configuration, the upper surface of the base housing 12 and the lower surface of the detachable optical housing 19 is contoured to accommodate index matching pillows 38 which are positioned along the optical path between the source 10 and the detector array 28. The index matching pillows 38 are comprised of very thin sheets of material with an index matching fluid disposed therebetween. The pillows are located in suitable depressions in the upper surface of the housing 12. When the detachable optical housing 19 is disposed as illustrated in FIG. 3, the contours of the lower surface will receive the pillows 34 to form an intimate contact therewith. In this fashion, an alternative means for minimizing the deviation of the direction of the radiation path which occurs at the boundary between base housing 12 and the detachable optical housing 19 is provided.

Figure 4:
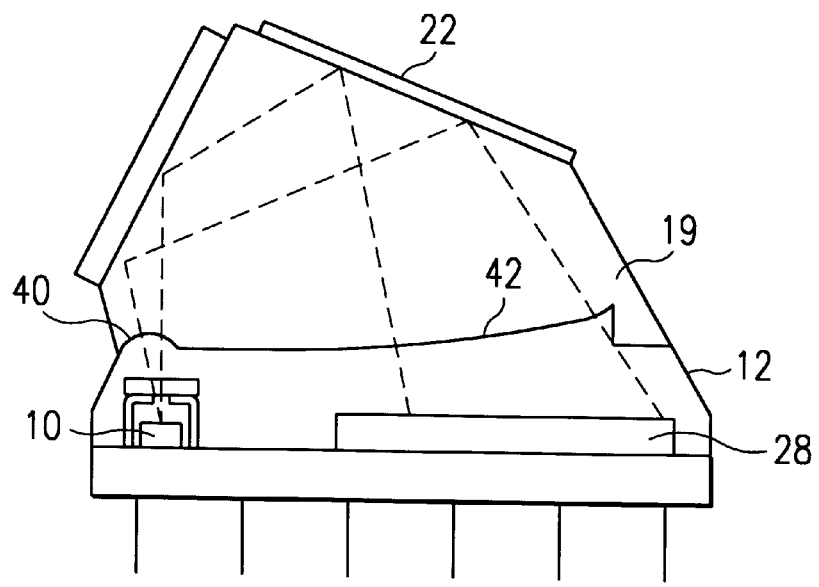
FIG. 4 illustrates another alternative sensor with curved surfaces at the boundary between the base and the detachable optical housing so that radiation passing therethrough is in a direction perpendicular to the base or optical housing.

A further means for minimizing the deviation of the direction of the radiation path which occurs at the boundary between base housing 12 and the detachable optical housing 19 is illustrated in FIG. 4. This configuration capitalizes on the fact that if a beam of light basses through a boundary in a perpendicular direction, the direction of the light beam will not be changed by passing through the intersection between the two regions with different indices of refraction. For this reason, the housing 12 is configured with an upper surface in the region 40 which is convex so that diverging radiation from the source 10 will pass through the upper surface of the housing 19 in a direction which is always perpendicular to the upper surface of the housing 19. In a similar fashion, the lower surface of the housing is made concave above region 40 so that the housing 19 and 12 will rest in intimate contact with each other. This will cause the radiation entering the housing 19 to pass through the surface thereof in a direction perpendicular to the surface. This will result in minimizing the deviation of the direction of the radiation path which occurs at the boundary between base housing 12 and the detachable optical housing 19.

The housing 12 has a concave portion 42 which is located in the optical path between the SPR surface 22 and the detector 28. The lower surface of the housing 19 is correspondingly convex. The curves are selected so that the radiation passing therethrough will be perpendicular to the surface of the housings 12 and 19 thereby providing an alternative means for minimizing the deviation of the direction of the radiation path which occurs at the boundary between base housing 12 and the detachable optical housing 19.

Figure 5:
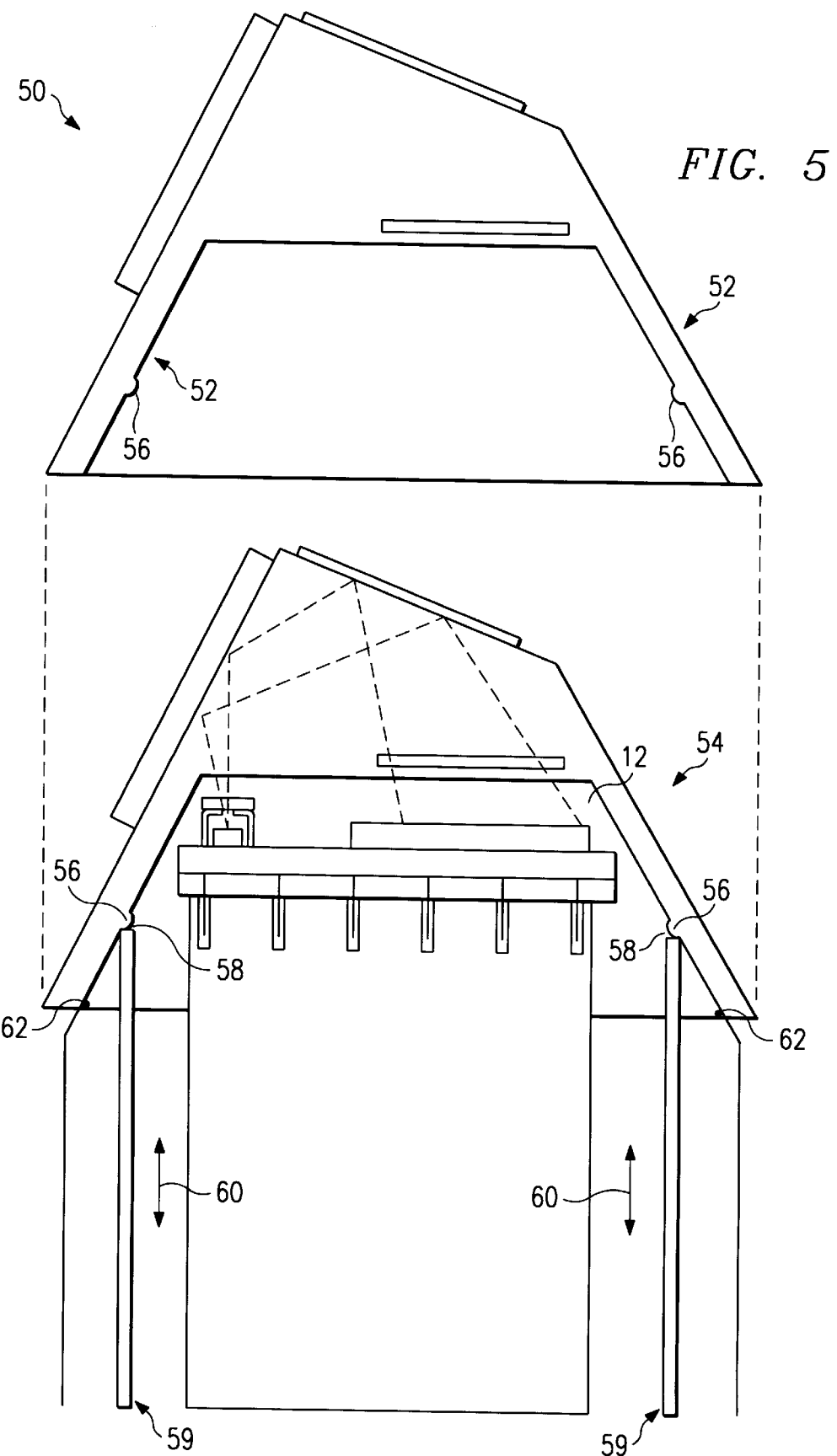
FIG. 5 illustrates a detachable optical housing and a complimentary base with a mechanism provided for securing the optical housing to the base.

A further alternative configuration is illustrated in FIG. 5. In this configuration, a detachable optical element is illustrated generally at 50 which has generally the same configuration of the detachable housing 19 of FIG. 1. The optical element 50 includes a mirror, SPR conductive film, a spectral filter and a body made of a material transparent to the radiation which is generated in the base housing 12. The optical element 50 additionally includes a downwardly projecting portion 52 which serves to align the element 50 with the base housing 12 when they are interfitted together as illustrated generally at 54. The inner surface of the projecting portion 52 has a plurality of inwardly projecting protrusions 56 which are positioned to interfit with indentations 58 on the outwardly facing surfaces of the base housing 12. In this manner, the optical element 50 can be affixed to the base housing 12.

A pair of push rods 59 are vertically movable within the base housing 12 in a direction indicated by the double headed arrows 60. When the push rods 59 are pushed upwardly, they engage the detachable optical element 50 in the region of the protrusions 56 and serve to disengage the element 50 from the base housing 12. When the push rods 59 are lowered, an optical element 50 can be affixed to the base housing 12 in a manner as described above.

As noted above, an index matching fluid is usually applied between the detachable optical element 50 and the base housing 12. The arrangement illustrated in FIG. 5 includes a gasket 62 disposed between the detachable optical element 50 and the base housing 12 to retain the index matching fluid therebetween when the element 50 and the housing 12 are pressed together. The other methods described above for 51 retaining the index matching fluid between these members can also be utilized in the configuration of FIG. 5.

The above description has been made with particular emphasis on the structure of the alternative embodiments illustrated in the attached drawings. It will be r recognized by those of skill in the art, however, that the above mentioned and other modifications to the structure of the invention can be made without departing from the spirit and scope of the invention as defined in the following claims.

What is claimed is:

1. A surface plasmon detector with interchangable optical elements comprising, in combination:

a source of optical radiation disposed on a base;

a sensor array sensitive to said optical radiation disposed on said base;

means for encapsulating said source of radiation and said sensor in a material which is capable of transmitting optical radiation from said source;

a detachable optical housing detachably coupled to said base, said housing made of a material which is capable of transmitting radiation from said source;

a film of a conductive material capable of sustaining surface plasmon resonance, said film being disposed on an exterior surface of said optical housing;

at least one optically reflective surface disposed on an exterior surface of said optical housing;

said optical reflective surface, said film and said housing being shaped and positioned relative to said source, sensor array and base so that radiation from said source is reflected by said film and said optically reflective surface and detected by said sensor array;

a path discontinuity minimizing means for minimizing the deviation of the direction of the radiation path which occurs at the boundary between said base and said detachable optical housing;

a polarizer disposed between said source and said sensor array to polarize the optical radiation which strikes said sensor array; and a filter disposed between said source and said sensor to prevent optical radiation at the frequency absorbed thereby from striking said sensor array.

2. A surface plasmon detector with interchangable optical elements comprising, in combination:

a source of radiation disposed on a base;

a sensor array disposed on said base;

an encapsulation of said source of radiation and said sensor in a material which transmits radiation from said source;

a detachable optical housing detachably coupled to said base, said housing made of a material which transmits radiation from said source;

a film of a conductive material capable of sustaining surface plasmon resonance, said film being disposed on an exterior surface of said optical housing, said optical housing and said film being shaped and positioned so that radiation from said source is reflected by said film and detected by said sensor array; and a path discontinuity minimizing means for minimizing the deviation of the direction of the radiation path which occurs at the boundary between said base and said detachable optical housing.

3. The surface plasmon detector of claim 2 wherein said path discontinuity minimizing means includes an index matching material disposed between said base and said housing.

4. The surface plasmon detector of claim 2 wherein said path discontinuity minimizing means includes contouring of the surfaces of said base and said housing so that any radiation from said source passes through the surfaces of said base and said housing in a direction substantially normal to the surface through which it passes.

5. The surface plasmon detector of claim 2 wherein said housing is contoured to interfit with said base which will hold said housing and said base together yet through deformation of said housing, said base or both said housing and said base permits separation of said housing from said base.

6. The surface plasmon detector of claim 3 additionally includes pockets disposed on either said housing or said base for holding said index matching fluid.

7. The surface plasmon detector of claim 3 additionally including a fluid retaining member retaining said index matching fluid between said base and said housing.

8. The surface plasmon detector of claim 2 wherein said housing and said base are shaped in a complementary fashion so that they are self aligning when they are interfitted.

9. The surface plasmon detector of claim 3 wherein said index matching fluid is contained in a flexible pouch disposed between said base and said housing.

10. The surface plasmon detector of claim 2 additionally including an optical filter disposed along the radiation path from said source to said detector to filter the radiation striking said sensor array in selected frequency ranges.

11. The surface plasmon detector of claim 2 additionally including a polarizer disposed along the radiation path from said source to said detector to polarize the radiation striking the sensor array.

12. The surface plasmon detector of claim 2 additionally including a housing disposed around said source with an aperture therethrough.

13. The surface plasmon detector of claim 2 additionally including means for separating said housing from said base.

* * * * *